United States Patent [19]

Bloch et al.

[11] 4,323,695

[45] Apr. 6, 1982

[54] PROCESS FOR MAKING AN ACRYLIC MONOMER

[75] Inventors: Bertrand Bloch, Paris; Chantal C. Meyer, Voisins le Bretonneux; Denis Charrier, Antony, all of France

[73] Assignee: Office National d'Etudes et de Recherches, Chatillon Sous Bagneux, France

[21] Appl. No.: 102,389

[22] Filed: Dec. 11, 1979

[30] Foreign Application Priority Data

Dec. 15, 1978 [FR] France ................. 78 35458

[51] Int. Cl.³ ............................................. C07C 67/14
[52] U.S. Cl. .................... 560/145; 560/181; 562/598; 260/544 Y; 526/245
[58] Field of Search ............... 560/145, 176, 181, 130, 560/211, 219; 562/599, 598

[56] References Cited

U.S. PATENT DOCUMENTS

| | | | |
|---|---|---|---|
| 2,948,725 | 8/1960 | Duschinsky et al. | 560/181 |
| 3,600,431 | 8/1971 | Taylor et al. | 560/146 |
| 3,669,998 | 6/1972 | Munekata et al. | 560/145 |
| 4,165,438 | 9/1979 | Schneider | 560/211 |

FOREIGN PATENT DOCUMENTS

| | | | |
|---|---|---|---|
| 48-31085 | 9/1973 | Japan | 560/598 |
| 924648 | 4/1963 | United Kingdom . | |
| 949904 | 2/1964 | United Kingdom . | |

OTHER PUBLICATIONS

Weygand et al., Preparative Organic Chemistry, pp. 243–247 and 378–379 (1972).

Kittila, Dimethylformamide Chemical Uses, p. 68 (1967).

Gault et al., as cited in Chem. Abstracts 70, 105896v (1969).

*Primary Examiner*—Joseph E. Evans
*Attorney, Agent, or Firm*—Larson and Taylor

[57] ABSTRACT

The invention relates to a novel process for making phenyl fluoroacrylate monomer. The monomer is obtained by reaction of a fluoroacrylic salt with an halogenating agent, followed by condensation of the fluoroacryloyl halogenide with phenol and recovery of the phenyl fluoroacrylate. The obtained monomer is applicable to the manufacture of transparent polymers of high thermal stability.

9 Claims, 3 Drawing Figures

PROCESS FOR MAKING AN ACRYLIC MONOMER

The invention relates to an acrylic derivative and more particularly to a process for synthesizing this derivative.

It is known that acrylic derivatives are generally polymerised easily and result in polymers of which a good number possess, in particular, properties of transparency and of mechanical strength of great interest. These polymers are then more particularly used as organic glasses, the most widely known in this respect being polymethyl methacrylate. However the field of use of these polymers is limited by their softening point which, in the case of polymethy methacrylate or PMMA, for example, is 95° C. It follows that the benefit of the properties mentioned above cannot be realized in high temperature uses.

The study of novel monomeric acrylic derivatives, leading to transparent materials useful at high temperature, therefore has great interest. But for exploitation on a large scale, it is indispensable to have monomeric products available which are easily synthesizable both from the point of view of the manipulations to be carried out and of cost.

It is a particular object of the invention to provide a novel acrylic derivative enabling preparation of polymers which, whilst having the properties of transparency of acrylic polymers generally, possess a high softening point permitting their use at high temperature.

It is also an object to provide a process for the synthesis of this derivative whose application and cost permit exploitation on an industrial scale.

The acrylic derivative, according to the invention, is constituted by phenyl fluoroacrylate of the formula:

The search, by the inventors, for a process enabling phenyl fluoroacrylate to be produced with satisfactory yields has led to carrying out this synthesis from a salt of fluoroacrylic acid of the formula $CH_2=CF-COOM$ in which M represents a metallic cation.

In accordance with the invention, the salt applied is subjected to the action of a halogenating agent, more especially a chlorinating agent and the resulting fluoroacryloyl chloride $CH_2=CF-COOCl$ is condensed with phenol $C_6H_5OH$.

This process of synthesis is illustrated by the following reaction diagram (when a chlorinating agent is utilised).

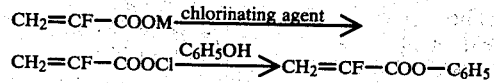

In the chlorination phase, the operation is carried out in a solvent medium, inert with respect to the chlorinating agent. Advantageously an agent playing the role of "catalyst", is added to the reaction medium, in particular dimethylformamide (DMF) and this, preferably in relatively large amounts, notably from 5 to 50%, preferably of the order of 25% in moles with respect to halogenating agent, notably chlorinating agent.

The chlorinating agent is advantageously selected from among the conventional agents, such as acid chlorides. A product such a thionyl chloride $SOCl_2$ is suitable. The solvent used may be constituted in this case by solvents such as chloroform or benzene.

The action of the chlorinating agent applied is advantageously exerted on a metallic salt of fluoroacrylic acid.

By reason of the convenience of synthesis and considering the yields obtained, the sodium salt is profitably resorted to or sodium fluoroacrylate of the formula:

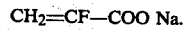

The use of the salt of fluoroacrylic acid and of the chlorinating agent in substantially stoichiometric amounts lead to the formation of fluoroacryloyl chlorides with high yields.

The reaction of forming the fluoroacryloyl chloride can be completed by a short reflux.

The second phase of the process, namely, the condensation with the phenol, is advantageously carried out in the reaction medium including the fluoroacryloyl chloride, without it appearing necessary to isolate the latter. The production in situ of condensation between the chloride and the phenol, which also permits simplification of handling involved in the application of the process also contributes favourably to the improvement in the general yield.

On the addition of the phenol, the simultaneous addition of a proton-accepting base is advantageously followed. Suitable bases in this respect comprise triethylamine.

To improve the accomplishment of the desired condensation, it proves useful to apply the various reactants in stoichiometric proportions.

The phenyl fluoroacrylate is collected from the reaction mixture, advantageously freed previously from unreacted reactants such as triethylamine or phenol. It appears convenient to recover the product by a technique such as distillation.

By means of the above features, the phenyl fluoroacrylate is obtained with satisfactory yields for industrial exploitation, whilst resorting to manipulations which are easily handled.

This acrylic derivative possess a high reactivity. Advantageously, it is easily polymerised, more especially by a free radical polymerisation process leading to polymers possessing valuable mechanical and optical properties even at high temperatures. These polymers may in fact possess softening points ranging up to about 170° C. which permits their use in particular in the acronautical industry, and more especially in the field of supersonic aircraft notably for the construction of windows and canopies.

For the manufacture more especially of the above polymeres, phenyl fluoroacrylate is advantageously used having a high degree of purity.

The crude product obtained at the end of the above-mentioned process is then subjected for this purpose to at least one purification treatment.

Particularly effective treatments comprise chromatography on a column and distillation, more especially fractional distillation of the monomer.

The production of products of high purity may also be carried out by fractional recrystalisation from the molten state without the use of solvent.

In fact, it is noticed that the phenyl fluoroacrylate monomer crystallises at temperature of the order of +4° C., slightly less than ambient temperature. This crystallisation occurring very slowly, it is possible to accelerate the process, for example to initiate solidification by means of seeds or by means of intense cooling.

The association of several purification methods enables the degreee of purity of the monomer to be considerably improved.

In particular, it is advantageous to resort successively to at least one fractional distillation operation and to at least one fractional recrystallisation operation.

The fractional distillation is advantageously carried out on a plate column until the production of a monomer having a degree of purity of at least 98%. To this end, it is particularly effective to resort to a column of about ten plates.

The following of the purification treatment by at least one fractional recrystallisation, with the removal at each repetition of the mother-liquors, enables a purity to be reached in practice of close to 100%.

In particular, the thus purified fluoroacrylate no longer includes phenol detectable by liquid phase chromatography and is found to be practically devoid of phenyl fluoroacetate, unless this is possibly present in trace amount.

The salt of fluoroacrylic acid used in the above-described synthesis is prepared from an alkyl ester of fluoroacetic acid of the formula $FCH_2$—COOR in which R represents an alkyl radical.

The process to which recourse is had comprises: in a first phase, the reaction in the presence of a base $M_1OR$ such as an alkali alcoholate, of the fluoroacetic ester $FCH_2$—COOR indicated above, with an alkyl ester of oxalic acid, of the formula R—O—CO—CO—OR, in which R is an alkyl radical identical or different from that of the fluroacetic ester;

In a second phase, the reaction with formaldehyde, or a compound which is a precursor of the latter, advantageously paraformaldehyde, of the enolate of the oxalofluoroacetic ester obtained of the formula RO—CO—CO(OM$_1$)=C(F)CO—OR in which R has the meaning already given and $M_1$ is a metallic cation coming from the alcoholate used in the first phase.

According to an advantageous feature of the invention, in a third phase, the saponification with a strong base of the reaction mixture, which enables the salt of the fluoroacrylic acid desired to be available without having to isolate the intermediate alkyl fluoroacrylate.

For practicing this additional feature of the invention, it is advantageous to resort, as the alkyl ester of fluoroacetic acid, to ethyl fluoroacetate F—CH$_2$—COO—C$_2$H$_5$, by reason of its reactivity and moreover of its availability on the market.

In the first phase of the process, the ethyl fluoroacetate is added to a reaction mixture comprising the product of the reaction of an alkyl ester and of oxalic acid with an alkali alcoholate.

For the formation of this product, advantageously an ester of oxalic acid available in commerce is used such as ethyl oxalate C$_2$H$_5$—COO—COO—C$_2$H$_5$. This oxalate is then treated with a basic salt, advantageously an alcoholate such as sodium ethylate C$_2$H$_5$—ONa.

The reaction between the oxalate and the ethylate is carried out conveniently by utilizing substantially equimolecular amounts of reactants.

Suitably, the oxalate is added to a solution or a suspension of the ethylate in an organic solvent, which is inert with respect to the reactants. This solvent may be selected from a wide range of products comprising notably, ethanol, ethyl ether, tetrahydrofurane, isopropyl oxide, butyl oxide, tetraline and xylene. However, it may be advantageous for what follows, in particular for the saponification (third phase) to use a water-miscible solvent such as ethanol, or tetrahydrofurane.

Among the useful solvents DMF is more particularly preferred. It enables actually the reaction mixture to be maintained fluid. Temperature control of the reaction is made easier. Furthermore it is possible to carry out the stirring for a longer time. It is easier as well to carry out the addition step with formaldehyde or paraformaldehyde.

As indicated above, to the thus constituted reaction mixture is added ethyl fluoroacetate, which leads to the formation of sodium enolate of oxalofluorocetic ester

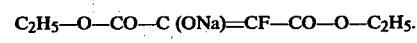

$C_2H_5$—O—CO—C(ONa)=CF—CO—O—C$_2$H$_5$.

This reaction works satisfactorily by using the ethyl fluoroacetate in amounts corresponding substantially to the stoichiometry of the reaction.

To introduce the acryloyl group into the molecule to be synthetised, recourse is had to condensation with formal; for this purpose paraformaldehyde is advantageously used.

The addition of the paraformaldehyde is advantageously carried out in the aforesaid reaction medium containing sodium enolate of oxalofluoroacetic ester, without proceeding, consequently, with the isolation of this enolate.

To improve the quality and the yield of the desired sodium fluoroacrylate, it is desirable to use an excess of paraformaldehyde with respect to equimolecularity. An excess of the order of 25 to 50% gives satisfactory results in this respect.

It also appears important to control the temperature, during the addition of paraformaldehyde, to a value below 60° C., preferably a value not exceeding 45° C.

The reaction of the enolate with paraformaldehyde is in fact rapid and distinctly exothermic. It can then lead, in the absence of temperature control, to too precocious gelling of the reaction medium, before the complete dissolution of the paraformaldehyde.

To obtain a complete reaction, it is desirable to ensure homogenous distribution of all of the paraformaldehyde introduced into the reaction medium, by stirring well before gelification, which can only be achieved if the spontaneous rise in temperature can be controlled so as not to result in too rapid a reaction velocity.

One of the means which can be used for this purpose consists of cooling, prior to the addition of the formaldehyde, the reaction medium to around 0° C. and not to allow the temperature in the course of the reaction to exceed 45° C. These conditions enable the production, with a good yield, of a product in which the proportion of double-bonds is close to the theoretical.

The addition product formed during this phase is then decomposed, in the course of a third phase, by saponification by means of a strong base. Experience shows that the addition of amounts of base corresponding substantially to the stoichiometry of the reaction enables satisfactory accomplishment of saponification.

The addition of the strong base, more especially soda, is advantageously carried out into the midst of the reaction medium.

An aqueous solution of the strong base will be resorted to and it will then be added to the reaction medium either directly in the case where this medium includes a water-soluble solvent or after having proceeded with the removal of the immiscible solvent, for example by evaporation, then after having added water to fluidise the medium.

Advantageously there follows a slow addition and, by cooling the reaction mixture, a temperature above or equal to 25° C. being nonetheless necessary to ensure complete saponification.

It is also desirable, to avoid any polymerisation at this stage of fluoroacrylic derivatives which are formed, to carry out the addition of the base in the presence of a polymerisation inhibitor. This inhibitor is advantageously selected from among those used customarily for this purpose in the field of acrylic derivatives and including for example hydroquinone or its derivatives.

In the course of this third phase, sodium oxalate precipitate is observed, a by-product of the reaction, very slightly soluble in water, which is separated, and the resulting solution is treated so as to recover the sodium fluoroacrylate that it contains.

To this end it is convenient to resort to evaporation of the solution.

The use of the above features enables sodium fluoroacrylate to be obtained with a practically quantitative yield and of a remarkable quality which is established to be of great importance for the yield of the reactions in which it is desired to utilise it subsequently.

According to an aspect of great interest, this derivative can be condensed with a large number of reactants and then constitutes a valuable precursor opening the way to very many syntheses of acrylic derivatives, its process of preparation as described enters into the scope of the invention.

Other characteristics and advantages of the invention will appear in the description of the Examples which follow and with the aid of the drawings, of which FIGS. 1 to 3 provide infrared and nuclear magnetic resonance (NMR) spectra characteristic of the product according to the invention.

EXAMPLE I

Preparation of sodium fluoroacrylate $CH_2=CF-COO\ Na$.

First a suspension of 76,85 g (1.13 mole) of sodium ethylate in 360 ml of tetrahydrofurane (THF) is prepared. The ethylate prepared by the action, on the stoichiometric amount of alcohol, of metallic sodium or sodium hydride (which permits the coloration of the sodium fluoroacrylate to be reduced) or again the commercial product, is used.

Working at ambient temperature 146 g (1 mole) of ethyl oxalate is then added slowly, and following this, 106 g (1 mole) of ethyl fluoroacetate.

The solution obtained is left to stand for 16 hours at room temperature. In this solution, first clear, a precipitate of sodium enolate of oxalofluoroacetic ester $C_2H_5-O-CO-C(ONa)=CF-CO-O-C_2H_5$ is formed.

According to a modification, the solution is heated for two hours at about 50° C.

To the suspension formed is then added, stirring well and at about 0° C. 45 g (1.5 mole) of paraformaldehyde. This addition is carried out rapidly, in one lot, the temperature rising spontaneously up to about 40° C., and the mixture gelling in some minutes. The temperature is held at 40—50° C. for a half an hour.

After cooling, the mixture is fluidified, by means of 600 ml of water containing about 0.5 g of hydroquinone as a polymerisation inhibitor, or better 0.5 g of monomethyl ether of hydroquinone, which enables a final practically colourless product to be obtained. It is then treated with 666 ml of aqueous 3 N NaOH added little by little. During this last treatment, which is exothermic, the temperature is held at 25° C. maximum by means of an ice bath. The sodium oxalate formed in the course of this saponification reaction is filtered and then the sodium fluoroacrylate isolated by extended evaporation of the solution, under vacuum and at 50° C. The residue is washed with alcohol and with acetone, and finally dried under vacuum at about 50° C. Yield 81%.

Elementary analysis in % by weight: C calc. 32.1: found 32.25; H calc. 1.8: found 1.71. Proportion of double bonds: calc. 100; found 96.4 (measured by the bromine index).

Alternatively, the process is carried on using the above conditions but by replacing THF by DMF—No gelification of the medium is observed—The obtained product is identical to the one indicated above.

EXAMPLE II

Preparation of phenyl fluoroacrylate $CH_2=CF-COO-C_6H_5$.

100 g (0.88 mole) of sodium fluoroacrylate is dispersed in 380 ml of benzene in the presence of 10 ml of dimethylformamide (DMF). 64.5 ml (0.9 mole) of thionyl chloride ($SOCl_2$) is added, and the the mixture is heated under reflux for 30 minutes. The fluoroacryloyl chloride then formed is not isolated, and is immediately treated in cold by resorting to an ice bath, with 84.5 g (0.9 mole) of phenol in the presence as hydrochloric acid accepting base, of 125 ml (0.9 mole) of triethylamine.

The mixture obtained is washed with 800 ml of water, to remove all the salts formed (sodium and triethylammonium chlorides) then, successively, with a solution of 52 ml of 1 N hydrochloric acid in 100 ml of water, and a solution of 105 ml of 3 N soda in 100 ml of water (in order to remove unreacted amounts of reactants) and finally, with water, until neutrality of the aqueous phase.

After evaporation of the organic phase and then rapid distillation, 110 g (0.65 mole) of crude phenyl fluoroacrylate are obtained, namely a yield of 60.3% calculated with respect to the ethyl fluoroacetate which has served for the preparation of the sodium fluoroacrylate. The crude product thus obtained is in the form of a liquid product at ambient temperature.

EXAMPLE III

Purification of phenyl fluoroacrylate monomer by fractional distillation of the crude product, followed by fractional recrystallisation.

A monomer obtained directly from a synthetic process according to that of Example II is utilised.

a —fractional distillation

The distillation is carried out on a ten plate column at a temperature of 40° C. under 0.25 mm of Hg (the temperature of the flask can however reach 120°–140° C. at the end of the operation) in the presence of monomethyl ether of hydroquinone as polymerisation inhibitor and sheltered from a too intense light.

At the head there generally passes a more or less yellow-coloured liquid, then the fractions become more and more colourless, without the temperature varying substantially. It is then fractionated as a function, not of temperature, but of colour.

Two fractions whose quantitative analyses are indicated in the following table I are collected (these analysis are carried out by the adjunction of an integrator—calculator, such as that marketed by LTT under the name ICAP5, to a liquid-phase chromatograph such as that marketed by Waters Associates under the name ALC/GPC 501.). Product as such is injected, or diluted to 100 mg/ml, the dilution solvent being identical with the elution solvent and constituted by a hexane/tetrahydrofuran mixture=99/1. For the filling of the column, the product marketed by Waters Associates under the name Durapak and which corresponds to the product marketed under the trademark Carbowax 400 grafted on silica, is used. The calibrations are carried out by means of pure phenol and fluoroacetate, diluted in a known manner.

TABLE I

| distillation fraction | Amount (g) | % by weight of monomer | % by weight of phenyl fluoroacetate | % by weight of phenol |
|---|---|---|---|---|
| 1 | 12.5 | 73.47 | 0 | 26.53 |
| 2 | 162 | 100* | 0 | 0* |
|   |     | 99.18** | 0 | 0.82** |

*Analysis of the fraction diluted to 100 mg/ml in Hexane/THF = 99/1
**Analysis of the crude fraction.

The results obtained show the high efficiency of this method which enables a completely colourless monomer to be obtained.

b —fractional recrystallisation

Below are reported the results obtained by recrystallising a monomer which has already been purified and this, more especially by fractional distillation on a 10 plate column as described previously.

The property of the monomer to crystallise at +4° C. is used and this is suceeded by the following general technique.

The monomer is placed in a tube, cooled to about −20° C. by plunging it into a bath constituted by a mixture of nitrogen liquid and trichloroethylene. Air is allowed to bubble into the mixture in the course of crystallisation for about 90 minutes, the temperature of the outer bath is then about −10° C. In a second stage, the uncrystallised fraction is filtered off, the temperature of the bath being at the end of filtration −5° C.

The results obtained after a series of fractional recrystallisations are indicated in Table II below:

TABLE II

| Analysed product | Amount (g) | % by weight of monomer | % by weight of phenyl fluoroacetate | % by weight of phenol |
|---|---|---|---|---|
| Starting product | 197.5 | 98.39 | 0.67 | 0.94 |
| Product of 1st recrystallisation | 133 | 99.82 | 0 | 0.17 |
| Product of 2nd recrystallisation | 126 | 100 | 0 | 0 |

Examination of these results shows that after the first recrystallisation, the ethyl fluoroacetate is completely removed and that, on the second recrystallisation, phenol is no longer detected.

The association of this recrystallisation operation with another purification method therefore has the advantage of leading to monomeric products of very great purity.

FIG. 1 provides an infrared absorption spectrum (variation of the transmission (T) in ordinates, as a function of the wave length in cm$^{-1}$) of the monomer according to the invention.

Figure 1:
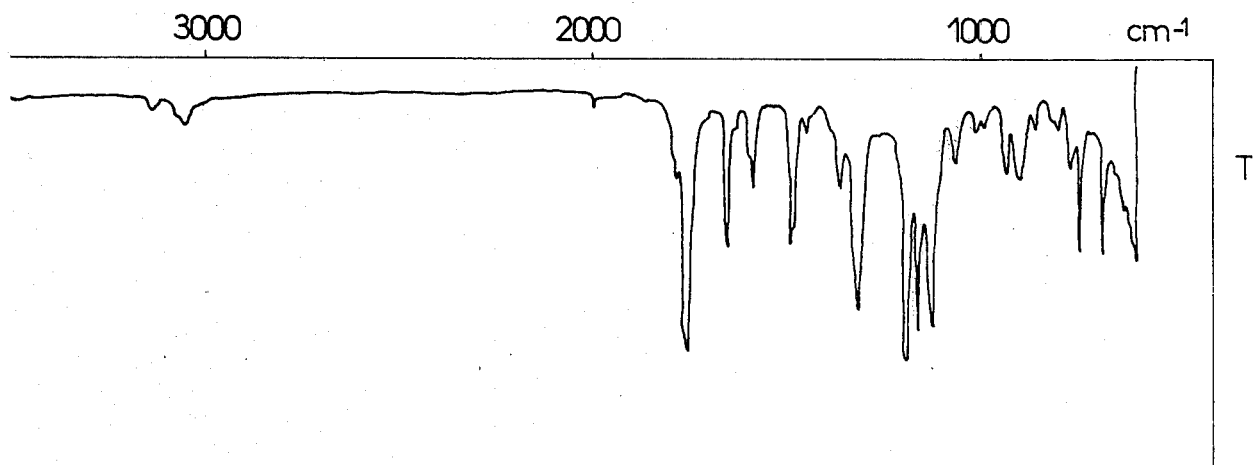
Figure 3:
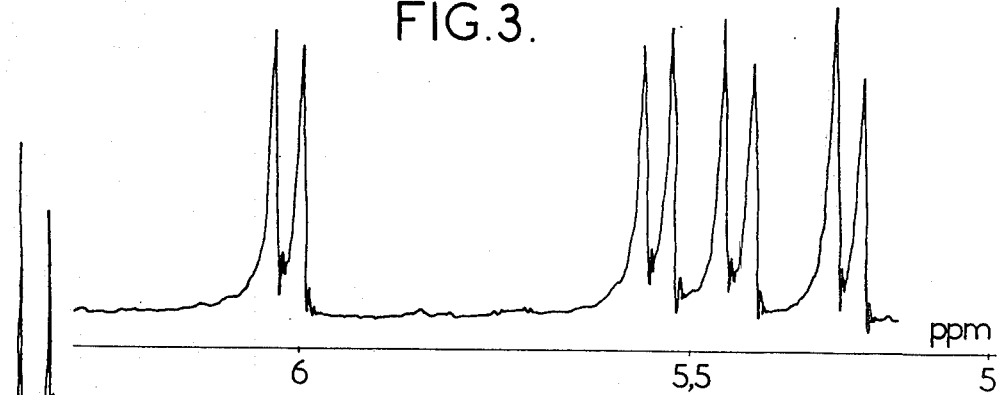
FIG. 3 is a portion an enlarged scale of this spectrum, for abscissa values of 5 to 6 ppm.
Figure 2:
FIG. 2 is an NMR spectrum of the proton in deuterated chloroform, at 90 MHz.

The product is characterised by a boiling point of about 42 C. under 26.66 Pascal. It crystallises at about +4° C. Its refractive index $n_D$ of the order of 1.17. The absorption spectrum in the infra red of the product is indicated in FIG. 1.

EXAMPLE IV

Manufacture of phenyl polyfluoroacrylate

A device comprising a tube of about 10 mm diameter connectable through a circular ramp to a vacuum or nitrogen circuit is used.

The monomer used is phenyl fluoroacrylate, previously preserved cold, in the crystallised state, in the absence of polymerisation inhibitor and containing less than 0.1% of impurity. Then to the tube about 8 g of liquid monomer and 0.2% of AIBN is introduced.

A first simultaneous cryodegasification operation of the sample follows by crystallisation in liquid nitrogen and then melting under vacuum, and two cryodegasification operations are then subsequently carried out.

After returning to room temperature, the tube is purged by repeated drainings and introductions of nitrogen.

The tube is then closed and plunged for 14 hours in a thermostatated bath at 35° C. for the polymerisation. After about 5 hours, gelling of the reaction masses is observed which become practically wholly solid after heating for about 14 hours.

The temperature is then gradually brought in 4 hours to 60° C. and held for about 1 hour. The sample is then completely solid, perfectly colourless and transparent.

The annealing phase follows operating under nitrogen and raising the temperature by 2° C./min up to 180° C. and then keeping it at this value for 30 minutes.

The softening point (Tr) is measured by penetrometry, using as a thermomechanical analyser that marketed under the name 941, by Du Pont de Nemours. It is observed that the polymer obtained has a softening point of 170° C.

We claim:

1. A process for producing phenyl fluoroacrylate by reacting a fluoroacryloyl halide with phenol to produce phenyl fluoroacrylate comprising the steps of:
saponifying the reaction product of formaldehyde and an enolate of an oxalofluoroacetic acid ester having the formula:

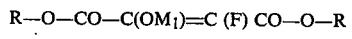

R—O—CO—C(OM$_1$)=C (F) CO—O—R in which R is an alkyl radical and M$_1$ is a metal cation, by using a substantially stoichiometric amount of a strong base in aqueous solution, and recovering the salt of fluoroacrylic acid thus obtained;

reacting substantially stoichiometric amounts of said salt with a halogenating agent in the presence of inert solvent with respect to the halogenating agent, and reacting the fluoroacryloyl halide with phenol.

2. A process according to claim 1, wherein said saponification is carried out at 25° C.

3. A process according to claim 1, wherein said formaldehyde is present in an amount of 25 to 50% in excess of an equimolar amount of said enolate.

4. A process according to claim 3 wherein said formaldehyde is reacted with said enolate without isolating said enolate from its reaction medium, and wherein the reaction between said formaldehyde and said enolate is maintained at less than 60° C.

5. A process according to claim 1, wherein said enolate is obtained by reacting an alkyl ester of oxalic acid of the formula R—O—CO—CO—O—R, wherein R is an alkyl radical, a base having the formula $M_1OR$ wherein $M_1$ is a metal cation and R is an alkyl radical, and an alkyl ester of fluoroacetic acid having the formula $FCH_2$—COOR wherein R is an alkyl radical, in a water miscible solvent which enables gelling of the reaction mixture to be avoided.

6. A process according to claim 5, wherein the water miscible solvent comprises dimethylformamide.

7. A process according to claim 1, wherein said base comprises sodium hydroxide.

8. A process according to claim 1, wherein R is ethyl and $M_1$ comprises sodium.

9. A process according to claim 2 wherein said strong base is provided in dilute aqueous solution.

* * * * *

UNITED STATES PATENT OFFICE
CERTIFICATE OF CORRECTION

PATENT NO. : 4,323,695
DATED : April 6, 1982
INVENTOR(S) : BLOCH ET AL

It is certified that error appears in the above-identified patent and that said Letters Patent are hereby corrected as shown below:

On the cover page of the patent, please correct the second inventor's name to read -- Chantal Cavalli nee Meyer --.

Signed and Sealed this

*Twelfth* Day of *October 1982*

|SEAL|

*Attest:*

*Attesting Officer*

GERALD J. MOSSINGHOFF

*Commissioner of Patents and Trademarks*